(12) United States Patent
Sethuraman et al.

(10) Patent No.: US 12,013,374 B2
(45) Date of Patent: Jun. 18, 2024

(54) BREAK STRENGTH METHOD FOR TESTING GLASS LASER CUT QUALITY OF DISC SUBSTRATES USING BREAK TESTING APPARATUS

(71) Applicant: Seagate Technology LLC, Fremont, CA (US)

(72) Inventors: Anand Venkatesh Sethuraman, Fremont, CA (US); Xinwei Li, Fremont, CA (US); Emil John C. Esmenda, San Jose, CA (US); Qui Tan, Hayward, CA (US); Ray Lilly, San Jose, CA (US); Koji Adachi, San Ramon, CA (US); Connor James Freeman, Long Beach, CA (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 491 days.

(21) Appl. No.: 17/380,414

(22) Filed: Jul. 20, 2021

(65) Prior Publication Data

US 2023/0021846 A1   Jan. 26, 2023

(51) Int. Cl.
*G01N 3/02* (2006.01)
*G01N 3/08* (2006.01)
*G01N 3/20* (2006.01)
*G01N 3/30* (2006.01)
*G01N 33/38* (2006.01)

(52) U.S. Cl.
CPC ............... *G01N 3/02* (2013.01); *G01N 3/30* (2013.01); *G01N 33/386* (2013.01); *G01N 2203/0062* (2013.01)

(58) Field of Classification Search
CPC ......... G01N 3/02; G01N 3/30; G01N 33/386; G01N 2203/0062; G01N 1/286; G01N 3/20; B23K 26/0624; B23K 26/0006; B23K 26/0622; B23K 26/53; B23K 26/38; B32B 17/06
See application file for complete search history.

(56) References Cited

U.S. PATENT DOCUMENTS

| 7,891,212 B2 | 2/2011 | Isono |
| 8,766,135 B2 | 7/2014 | Roh et al. |
| 9,134,171 B2 | 9/2015 | Blomster et al. |

(Continued)

FOREIGN PATENT DOCUMENTS

| JP | WO2005093720 A1 | 2/2008 |
| JP | 2012079363 A | 4/2012 |

(Continued)

*Primary Examiner* — Brandi N Hopkins
(74) *Attorney, Agent, or Firm* — Westman, Champlin & Koehler, P.A.

(57) ABSTRACT

A method includes forming, by a laser beam supplied by a laser cutting system, a laser-cut line in each of a plurality of glass samples. Each different laser-cut line in each different glass sample of the plurality of glass samples is formed when the laser cutting system is at a different process setting. The method also includes subjecting each of the plurality of glass samples with the laser-cut lines to a break test, and obtaining a plurality of break strength values. Each different break strength value of the plurality of break strength values is indicative of a laser-cut line quality of the respective glass sample of the plurality of glass samples.

20 Claims, 4 Drawing Sheets

(56) References Cited

U.S. PATENT DOCUMENTS

| | | | |
|---|---|---|---|
| 9,645,064 B1* | 5/2017 | Alam | G01N 3/30 |
| 9,938,180 B2 | 4/2018 | Abramov et al. | |
| 10,017,410 B2 | 7/2018 | Hosseini | |
| 10,947,148 B2 | 3/2021 | Ahner et al. | |
| 2006/0232403 A1 | 10/2006 | Dang et al. | |
| 2008/0241603 A1 | 10/2008 | Isono | |
| 2011/0129693 A1 | 6/2011 | Sono | |
| 2013/0291593 A1 | 11/2013 | Roh et al. | |
| 2013/0323469 A1* | 12/2013 | Abramov | B23K 26/364 |
| | | | 428/155 |
| 2015/0118522 A1 | 4/2015 | Hosseini | |
| 2015/0136743 A1* | 5/2015 | Hosseini | C03B 33/091 |
| | | | 219/121.61 |

FOREIGN PATENT DOCUMENTS

| | | |
|---|---|---|
| JP | 5959597 B2 | 8/2016 |
| KR | 101407976 B1 | 7/2014 |

* cited by examiner

BREAK STRENGTH METHOD FOR TESTING GLASS LASER CUT QUALITY OF DISC SUBSTRATES USING BREAK TESTING APPARATUS

SUMMARY

In one embodiment, a method is provided. The method includes forming a first laser-cut line in a first glass sample with a first laser beam supplied by a laser cutting system when the laser cutting system is at a first process setting. The method also includes forming a second laser-cut line in a second glass sample with a second laser beam supplied by the laser cutting system when the laser cutting system is at a second process setting. The method further includes subjecting the first glass sample with the first laser-cut line to a first break test, and obtaining a first break strength value. The method additionally includes subjecting the second glass sample with the second laser-cut line to a second break test, and obtaining a second break strength value. One of the first process setting or the second process setting is identified as a preferred process setting for the laser cutting system based on a comparison of the first and second break strength values.

In another embodiment, a break testing apparatus is provided. The break testing apparatus includes a disc-shaped support configured to support a glass sample. The glass sample has a laser-cut line. The break testing apparatus also includes a plunger configured to apply a break force generated by a force generation machine to the glass sample supported by the disc-shaped support.

In yet another embodiment, a method is provided. The method includes forming, by a laser beam supplied by a laser cutting system, a laser-cut line in each of a plurality of glass samples. Each different laser-cut line in each different glass sample of the plurality of glass samples is formed when the laser cutting system is at a different process setting. The method also includes subjecting each of the plurality of glass samples with the laser-cut line to a break test, and obtaining a plurality of break strength values. Each different break strength value of the plurality of break strength values is indicative of a laser-cut line quality of the respective glass sample of the plurality of glass samples.

This summary is not intended to describe each disclosed embodiment or every implementation of the break strength methodology for glass laser cut quality quantification. Many other novel advantages, features, and relationships will become apparent as this description proceeds. The figures and the description that follow more particularly exemplify illustrative embodiments.

DETAILED DESCRIPTION

Embodiments of the disclosure relate to quantifying a quality of a laser cut in a glass sheet.

Laser cutting machines are utilized in a wide range of industries to shape or cut parts during manufacturing. In the data storage industry, laser cutting machines may be utilized to cut disc substrates from glass sheets. The disc substrates are later coated with magnetic material to form data storage discs. The quality of a laser cut by the laser cutting machine influences disc substrate yield.

One prior technique for measuring the quality of a laser cut in a glass sheet involved, for example, inspecting the laser cut with a microscope. These inspections were repeated for numerous laser-cut glass samples for each different one of a number of different laser cutting process settings in the laser cutting machine to determine a best one of the different settings (e.g., a setting that produced the least defects). This was a laborious and time-consuming process.

In embodiments of the disclosure, laser lines are cut into different glass sheet samples, with a different process setting employed for the laser cutting machine when carrying out the laser cut into each different glass sheet sample. The different glass sheet samples with the different laser cuts are then each subjected to a break test, and break strength values are obtained for each of the different glass sheet samples. A process setting for the laser cut that results in the lowest of the different break strength values is a process setting that will produce a highest yield. Advantages of this process include greater accuracy with the use of a relatively small number of samples. Prior to providing details regarding the different embodiments, a description of an illustrative operating environment is provided below.

Figure 1B:
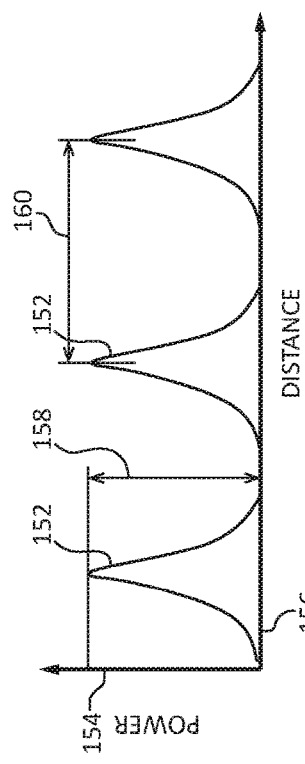
FIG. 1B is a graphical illustration showing laser pulses whose values may be adjusted based on break strength values determined in accordance with embodiments of the disclosure.
Figure 1A:
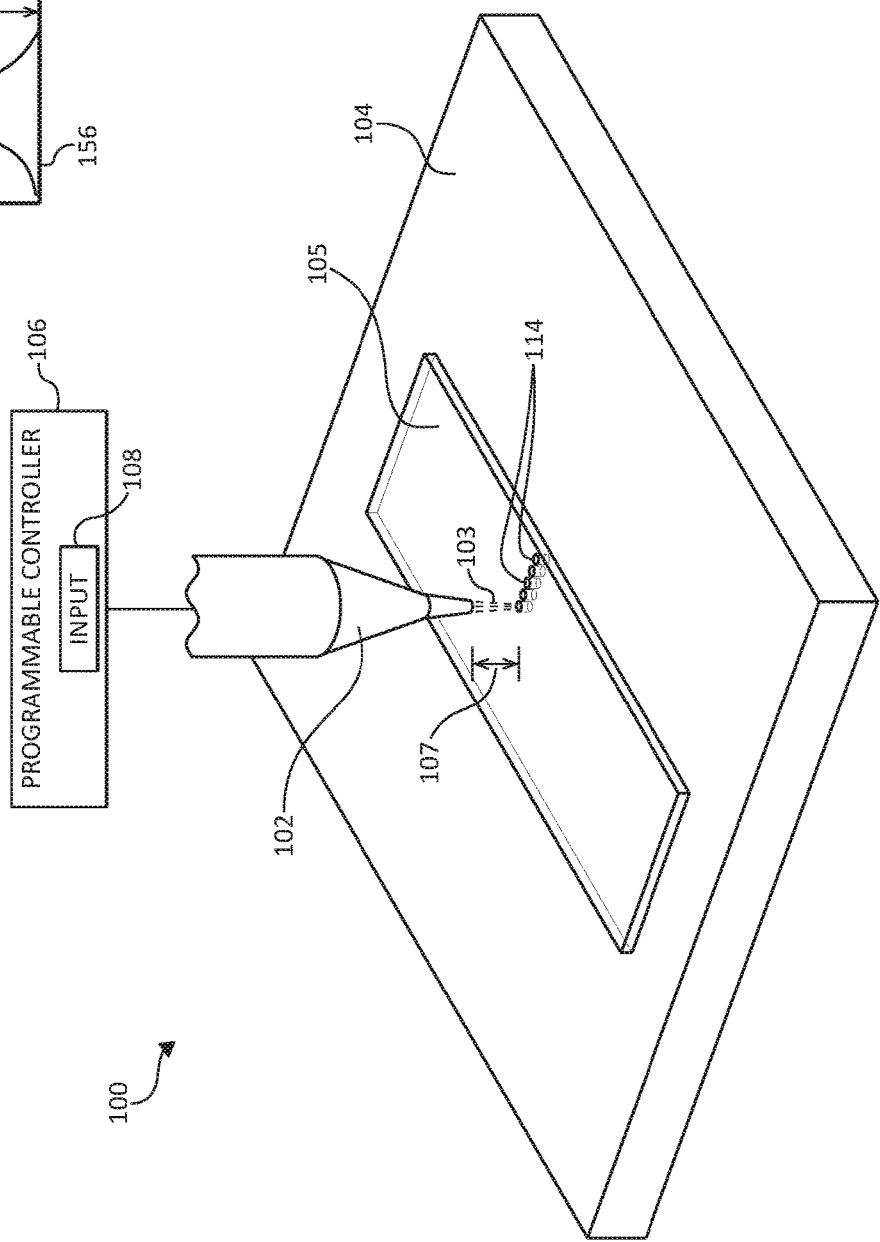
FIG. 1A is a diagrammatic illustration of a laser cutting machine/system whose process settings may be determined in accordance with embodiments of the disclosure.

FIG. 1A shows an illustrative operating environment in which process settings determined in accordance with embodiments disclosed herein may be employed. The operating environment shown in FIG. 1A is for illustration purposes only. Embodiments of the present disclosure are not limited to any particular operating environment such as the operating environment shown in FIG. 1A. Embodiments of the present disclosure are illustratively practiced within any number of different types of operating environments.

It should be noted that like reference numerals are used in different figures for same or similar elements. It should also be understood that the terminology used herein is for the purpose of describing embodiments, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps of the embodiments thereof. For example, "first," "second," and "third" elements or steps need not necessarily appear in that order, and the embodiments thereof need not necessarily be limited to three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," "intermediate" and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

It will be understood that, when an element is referred to as being "connected," "coupled," or "attached" to another element, it can be directly connected, coupled or attached to the other element, or it can be indirectly connected, coupled, or attached to the other element where intervening or intermediate elements may be present. In contrast, if an element is referred to as being "directly connected," "directly coupled" or "directly attached" to another element, there are no intervening elements present. Drawings illustrating direct connections, couplings or attachments between elements also include embodiments, in which the elements are indirectly connected, coupled or attached to each other.

FIG. 1A is a diagrammatic illustration of a laser cutting machine/system 100 whose process settings may be determined in accordance with embodiments of the disclosure. Laser cutting system 100 may include a laser 102, a working table 104, and a programmable controller 106 that may include an input 108 via which different process settings may be entered/adjusted. In the interest of simplification, elements such as power supply circuitry, laser 102 positioning elements, etc., are not shown.

Laser 102 may include a laser source (e.g., a resonator (not shown)) that creates a laser beam. Laser 102 may also include a transport fiber (not shown) or mirrors (not shown), in a machine head, that conduct the laser beam. The machine head may also include a lens (not shown) that focuses the laser beam at a high power on a very small diameter spot/area. The focused laser beam is denoted by reference numeral 103 in FIG. 1A. In some embodiments, laser 102 is a pulsed laser in which optical power of the laser beam 103 appears in pulses having an adjustable duration and repetition rate. In other embodiments, laser 102 may be a continuous-wave laser that produces a continuous, uninterrupted laser beam. The examples provided below primarily relate to pulsed laser systems.

FIG. 1B is a graphical representation 150 of example pulses 152 in a pulsed laser system. In FIG. 1B, a vertical axis 154 represents power, and a horizontal axis 156 represents distance. As will be described below, a pulse peak power 158 of the pulses 152, and a pulse peak-to-peak spacing (or stitch spacing) 160 may be adjusted to improve/refine a laser cutting process. In general, adjustments to the different process settings may be carried our via programmable controller 106 of FIG. 1A.

Programmable controller 106 may include one or more processors or microprocessors (not shown) and one or more memories (not shown) that are communicatively coupled to the processors, and may store instructions for execution by the processors. Further, the memories may store process settings such as the pulse peak power 158, the pulse peak-to-peak spacing 160, etc. Process settings values may be entered/adjusted via input 108. For example, a user may enter process settings using a keypad of input 108, adjust process settings by turning a knob, or pressing one or more buttons, etc. Alternatively, the user may input/adjust processing setting values from a device that is external to laser cutting system 100, and that is capable of wired/wireless communication with laser cutting system 100. An example of an external device may be a handheld mobile device that is capable of receiving process setting values input by a user into the device, and communicating those values to the laser cutting system 100. In general, any suitable technique may be employed to input/adjust process setting values. It should be noted that, in addition to the pulse peak power 158 and the pulse peak-to-peak spacing 160, other process settings such as laser 102 z-height 107 above a glass sample 105 may be adjusted manually or with the help of controller 106.

Working table 104 may support, convey, and/or fix a glass sheet sample 105 to be cut by laser 102. In one embodiment, flatness of the glass sample 105 is maintained during cutting by laser 102 due to the nature of the process. Accordingly, the working table 104 is processed with high precision so as to have high flatness and may be formed of metal or marble for the highly precise process. The glass sheet sample 105 may be securely maintained in position on the working table 104 by the use of mechanical or vacuum chucking. In general, any suitable mechanism may be utilized to maintain the glass sheet sample in position on the working table 104.

During operation, the laser beam 103 is translated relative to the glass sheet sample 105, and the laser beam 103 melts and vaporizes portions 114 of the glass sheet sample 105 through its thickness. Portions or dots 114 are very closely spaced, and may be formed across the entire width of the glass sheet sample 105. Thereafter, the glass sheet sample 105 may be separated along the dots 114 by applying a force on the glass sheet sample 105 in the dotted region. In one example, the glass sheet samples 105 are each rectangular in shape measuring 60 millimeters (mm) in length, and having a width of 20 mm. The laser-cut line formed by dots 114 is 20 mm, which is the entire width of the rectangular glass sheet sample 105. The laser cut may be positioned in the middle of the sample 105 length (e.g., at 30 mm in the length direction), and may be formed with the laser beam 103 perpendicular to the glass sheet sample. In general, the glass sheet samples may have any suitable dimensions. Breaking of laser-cut glass sheet samples such as 105 is described further below in connection with FIGS. 4A-4C.

Figure 2:
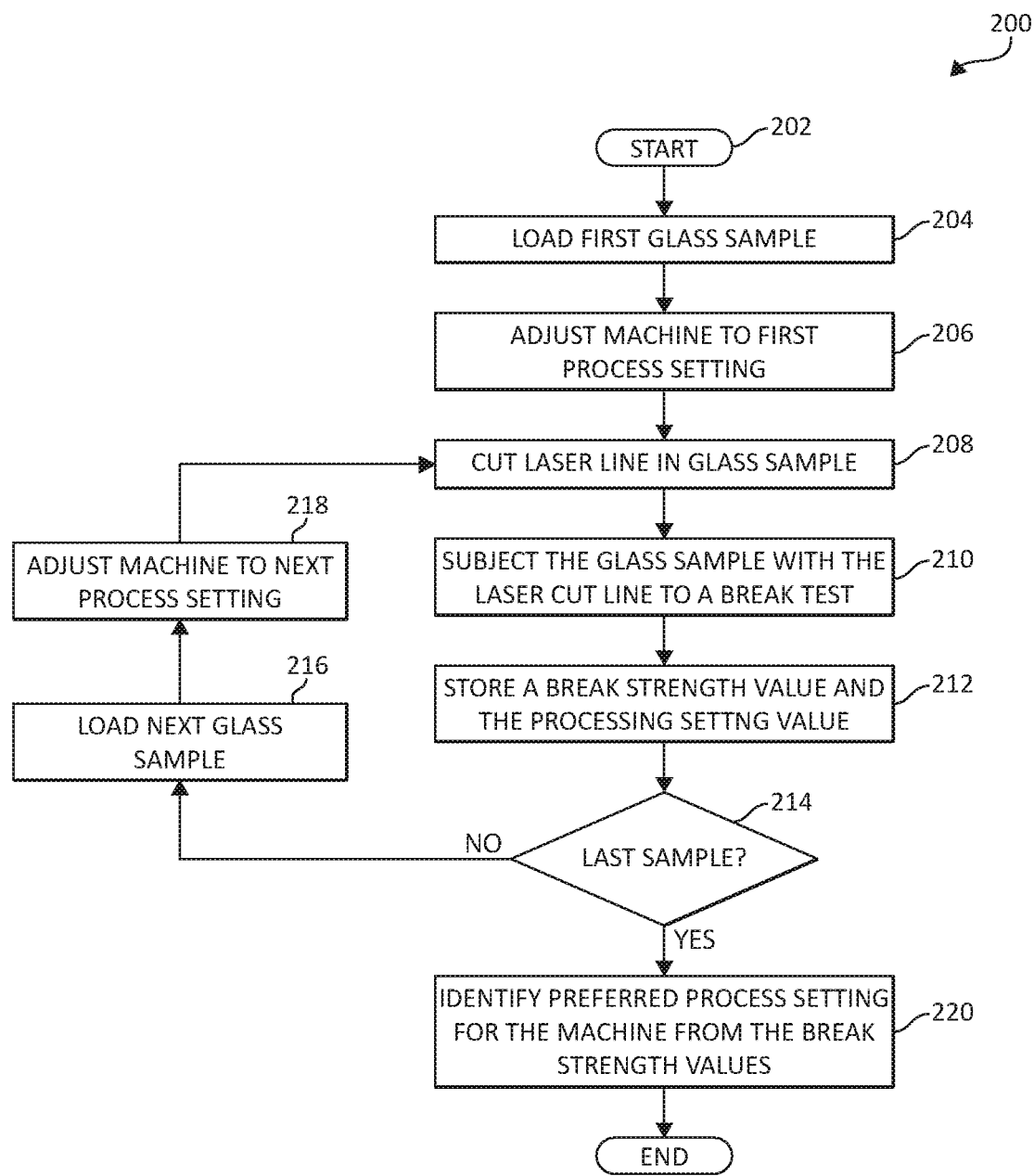
FIG. 2 is a flowchart of a method embodiment.

FIG. 2 is a flowchart of a method 200 of testing a glass laser cut quality in accordance with one embodiment. The method starts at 202. At 204, a first glass sheet sample is loaded into a laser cutting machine/system (e.g., 100 of FIG. 1). At 206, the laser cutting machine/system is adjusted to a first process setting. At 208, a laser line is cut into the glass sample by the laser cutting machine/system. At 210, the glass sample with the laser cut line is subjected to a break test. The break test may be carried out in any suitable break testing machine. One example of a break testing machine is described below in connection with FIGS. 4A and 4B. At 212, the first process setting (e.g., a first duration between consecutive laser beam pulses, a first laser power value, etc.) and the corresponding break strength value are stored. Alternatively, the first processing setting values may be stored at 206, and the corresponding break strength value may be stored at 212. At 214, a determination is made as to whether any more glass samples are to be cut and tested. If there are more glass samples to be cut and break tested, a next glass sample is loaded into the laser cutting machine/system at 216, and the machine's process settings are adjusted at 218 (e.g., the duration between consecutive laser beam pulses is changed, a laser power value is changed, etc.). The process then continues as illustrated in FIG. 2 until a break test is carried out on the last sample, and the process setting and break strength values are stored. Thereafter, at 220, a preferred process setting for the laser cutting machine is determined from the break strength values. In some embodiments, this may involve selecting a process setting that corresponds to the lowest break strength value of the different break strength values as the preferred process setting for the laser cutting machine/system.

It should be noted that the order shown in FIG. 2, which involves laser cutting one glass sample and then breaking that sample before laser cutting another glass sample, is only one example of a cutting and breaking order. In an alternate example, the laser cutting of all glass samples may be carried out first, followed by the break testing of all the already-cut glass samples. In general, any suitable order may be employed in different embodiments.

Figure 3:
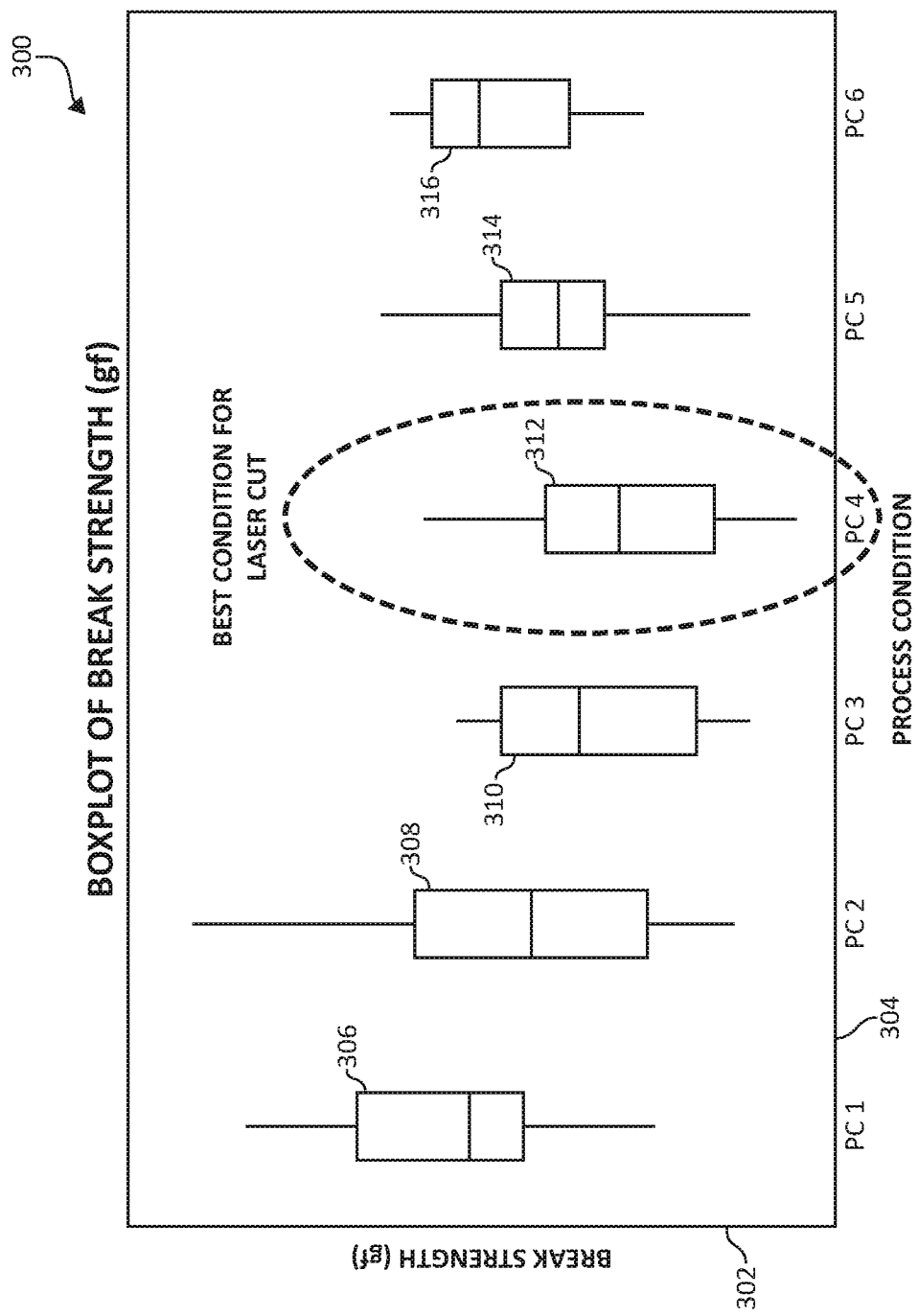
FIG. 3 is a graphical representation of determining a glass laser cut quality in accordance with one embodiment.

FIG. 3 is a graphical representation 300 of determining a glass laser cut quality in accordance with one embodiment. In FIG. 3, a vertical axis 302 represents break strength in gram-force (gf), and a horizontal axis 304 represents different process conditions (PC1-PC6). Box plots 306, 308, 310, 312, 314, and 316 are for process conditions PC1, PC2, PC3, PC4, PC5, and PC6, respectively. From FIG. 3, it is seen that PC4 produces a laser-cut line in a glass sample which breaks with a least break strength of the 6 glass samples with laser-cut lines. Thus, PC4 is a best of the 6 process conditions for the laser cutting machine/system.

Figure 4B:
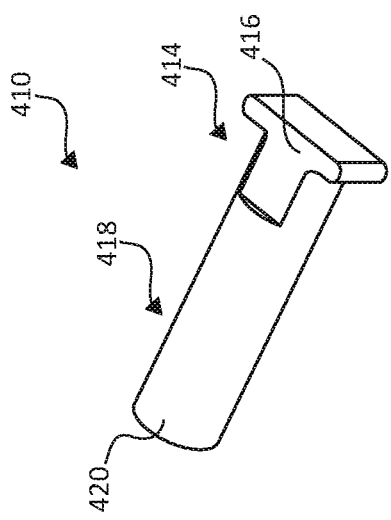
FIG. 4B is a perspective view of a plunger in accordance with an embodiment of the disclosure.
Figure 4C:
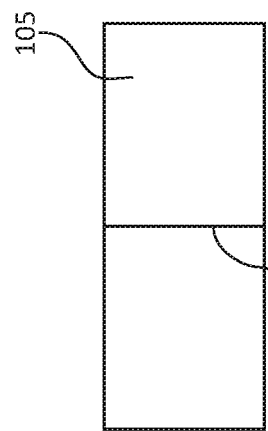
FIG. 4C is a top view of a laser-cut glass sample utilized in embodiments of the disclosure.
Figure 4A:
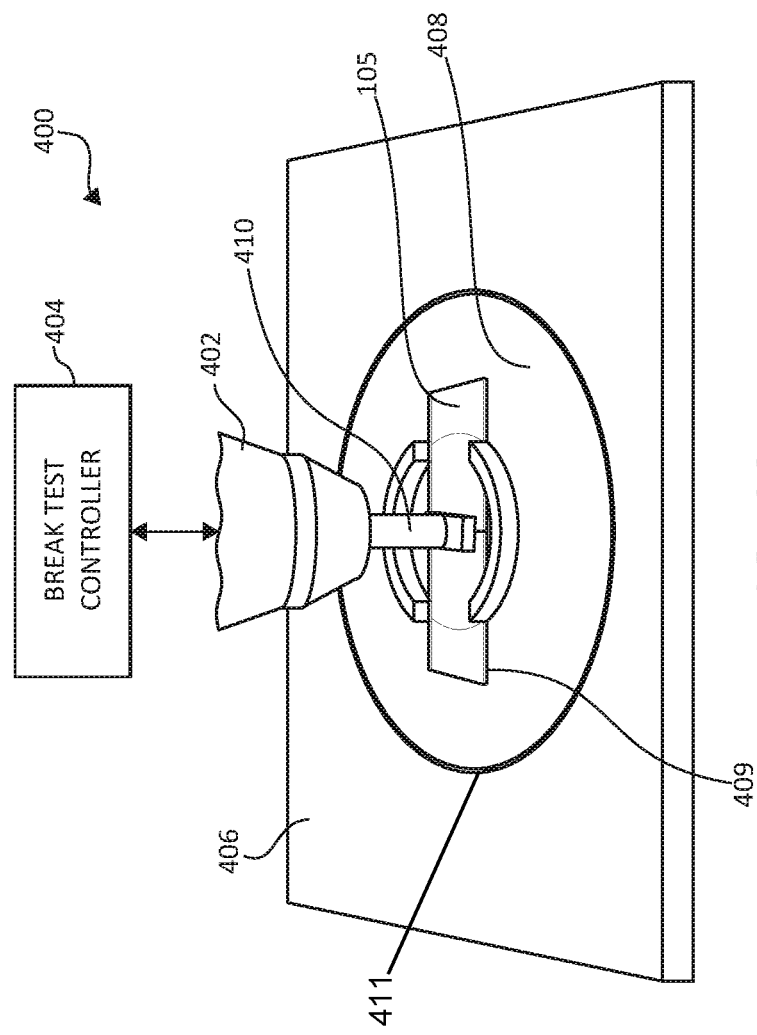
FIG. 4A is a diagrammatic illustration of a break testing apparatus that includes a glass sample support and a plunger in accordance with embodiments of the disclosure.

FIG. 4A is a diagrammatic illustration of a break testing apparatus 400 that includes a glass sample support 408 and a plunger 410 in accordance with embodiments of the disclosure. FIG. 4B is a perspective view of the plunger 410. Break testing apparatus 400 includes a force generation machine 402, a break test controller 404, a disc substrate support 406, glass sample support 408 and plunger 410.

Break testing apparatus 400 is adapted to shift from being used for break testing data storage disc substrates (not shown) to break testing glass sheet samples (e.g., rectangular glass sheet samples such as 105 described above in connection with FIG. 1A). When apparatus 400 is utilized as a break testing machine for testing data storage disc substrates, the data storage disc substrate is inserted into a slot 411 of disc substrate support 406 (in place of glass sample support 408), and a plunger with a shape that is different from the shape of plunger 410 is attached to force generation machine 402 for break testing the data storage disc substrates. However, for glass sheet sample 105 testing, glass sample support 408, which is disc-shaped, takes the place of the data storage disc substrate within disc substrate support 406. Also, plunger 410, which is suitable for breaking laser-cut glass sample 105, is attached to force generation machine 402.

In general, disc-shaped support 408 includes a rectangular slot 409 that is configured to receive and support the rectangular glass sheet sample 105. Plunger 410 is configured to apply a force generated by force generation machine 402 to the rectangular glass sheet sample 105 supported by the disc-shaped support 408. As can be seen in FIG. 4B, plunger 410 includes a first portion 414 that includes a first end 416 that is rectangular or square in shape. Also, plunger 410 includes a second portion 418 that may be cylindrical in shape in some embodiments, and includes a second end 420 that is configured to couple to the force generation machine 402.

As can be seen in FIG. 4A, plunger 410 is positioned over the rectangular glass sample 105 with the first end 416 of plunger 410 in contact with sample 105, such that force is applied on a portion of the sample 105 that includes laser-cut line 412 shown in FIG. 4C. It should be noted that although laser-cut line 412 is shown as a continuous line in FIG. 4C, line 412 may include closely-spaced laser-cut portions (e.g., dots 114) as shown in FIG. 1A.

A breaking testing operation may be initiated by a user by providing a test-initiation input to break test controller 404, for example. During operation, the rectangular/square first end 416 of plunger 410, which is in direct contact with the glass sheet sample 105, transfers a break force to the grass sheet sample 105. When a glass sample breaks, the break strength value may be stored in break test controller 404. Break strength values for different process setting values may be compared as described earlier in connection with FIG. 2, for example, and suitable processing settings for the laser cutting machine (e.g., laser cutting machine 100 of FIG. 1) are selected.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be reduced. Accordingly, the disclosure and the figures are to be regarded as illustrative rather than restrictive.

One or more embodiments of the disclosure may be referred to herein, individually and/or collectively, by the term "invention" merely for convenience and without intending to limit the scope of this application to any particular embodiment or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments include more features than are expressly recited in each claim. Rather, as the following claims reflect, inventive subject matter may be directed to less than all of the features of any of the disclosed embodiments.

The above-disclosed subject matter is to be considered illustrative, and not restrictive, and the appended claims are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:
1. A method comprising:
   forming a first laser-cut line in a first glass sample with a first laser beam supplied by a laser cutting system when the laser cutting system is at a first process setting;

forming a second laser-cut line in a second glass sample with a second laser beam supplied by the laser cutting system when the laser cutting system is at a second process setting;

subjecting the first glass sample with the first laser-cut line to a first break test, and obtaining a first break strength value;

subjecting the second glass sample with the second laser-cut line to a second break test, and obtaining a second break strength value; and identifying one of the first process setting or the second process setting as a preferred process setting for the laser cutting system based on a comparison of the first and second break strength values.

2. The method of claim 1, wherein a first incremental force is applied to the first glass sample during the first break test, and a second incremental force is applied to the second glass sample during the second break test.

3. The method of claim 2, wherein:
the first and second glass samples are rectangular glass sheet samples;
the first laser-cut line is in a width direction of the first rectangular glass sheet sample;
the first incremental force is applied at the first laser-cut line;
the second laser-cut line is in a width direction of the second rectangular glass sheet sample; and
the second incremental force is applied at the second laser-cut line.

4. The method of claim 1, further comprising selecting the first process setting as the preferred process setting for the laser cutting system when the first break strength value is less than the second break strength value.

5. The method of claim 1, wherein the first laser beam and the second laser beam are pulsed laser beams.

6. The method of claim 1, wherein the first process setting comprises a first peak-to-peak spacing between consecutive laser beam pulses for the first laser beam, and wherein the second process setting comprises a second peak-to-peak spacing between consecutive laser beam pulses for the second laser beam, and wherein the first peak-to-peak spacing is different from the second peak-to-peak spacing.

7. The method of claim 1, wherein the first process setting comprises a first pulse peak power for the first laser beam, and wherein the second process setting comprises a second pulse peak power for the second laser beam, and wherein the first pulse peak power is different from the second pulse peak power.

8. A break testing apparatus comprising:
a disc-shaped support configured to support a glass sample, the glass sample having a laser-cut line; and
a plunger configured to apply a break force generated by a force generation machine to the glass sample supported by the disc-shaped support, wherein the plunger comprises a substantially flat surface that is in contact with a surface of the glass sample when the break force is applied to the glass sample.

9. The break testing apparatus of claim 8, wherein the plunger comprises a first portion that comprises a first end that is rectangular or square in shape and comprises the substantially flat surface that is in contact with a surface of the glass sample when the break force is applied to the glass sample, and wherein the first end is configured to transfer the break force to the glass sample.

10. The break testing apparatus of claim 9, wherein the plunger further comprises a second portion that is cylindrical in shape and comprises a second end that is configured to couple to the force generation machine.

11. The break testing apparatus of claim 8, wherein the disc-shaped support comprises a rectangular slot configured to receive the glass sample, the glass sample being rectangular in shape.

12. The break testing apparatus of claim 8, wherein the disc-shaped support is configured to fit into a data storage disc substrate-receiving slot of a data storage disc substrate testing machine, thereby allowing for utilization of the data storage disc substrate-receiving slot for both data storage disc substrate testing and glass sample testing.

13. A method comprising:
forming, by a laser beam supplied by a laser cutting system, a laser-cut line in each of a plurality of glass samples, wherein each different laser-cut line in each different glass sample of the plurality of glass samples is formed when the laser cutting system is at a different process setting; and
subjecting each of the plurality of glass samples with the laser-cut line to a break test, and obtaining a plurality of break strength values, wherein each different break strength value of the plurality of break strength values is indicative of a laser-cut line quality of the respective glass sample of the plurality of glass samples.

14. The method of claim 13, further comprising identifying one of the plurality of different process settings as a preferred process setting for the laser cutting system based on a comparison of the different break test values of the plurality of break strength values.

15. The method of claim 14, further comprising selecting the one of the plurality of different process settings corresponding to the lowest break strength value of the plurality of break strength values as the preferred process setting for the laser cutting system.

16. The method of claim 13, wherein a different incremental force is applied to each different glass sample of the plurality of glass samples during each different break test of the break tests to determine the plurality of break strength values.

17. The method of claim 16, wherein:
each glass sample of the plurality of glass samples is a rectangular glass sheet sample;
each laser-cut line is in a width direction of each rectangular glass sheet sample of the plurality of rectangular glass sheet samples; and
each different incremental force is applied at the respective laser-cut line of the corresponding rectangular glass sheet sample.

18. The method of claim 13, wherein the laser beam is a pulsed laser beam.

19. The method of claim 18, wherein the different process settings comprise different peak-to-peak spacings between consecutive laser beam pulses for the laser beam.

20. The method of claim 19, wherein the different process settings comprise different peak pulse power settings for the laser beam.

* * * * *